(12) United States Patent
Montano

(10) Patent No.: US 12,141,733 B2
(45) Date of Patent: Nov. 12, 2024

(54) METHOD AND SYSTEM FOR ASSEMBLING AND COMPLETING A COLLECTION OF INDIVIDUAL DISPARATE-SHAPED COMPONENTS WITH IDENTIFICATION VIA ELECTRONIC IMAGES

(71) Applicant: Robert A Montano, Laramie, WY (US)

(72) Inventor: Robert A Montano, Laramie, WY (US)

( * ) Notice: Subject to any disclaimer, the term of this patent is extended or adjusted under 35 U.S.C. 154(b) by 448 days.

(21) Appl. No.: 16/628,919

(22) PCT Filed: Jul. 6, 2018

(86) PCT No.: PCT/US2018/041156
§ 371 (c)(1),
(2) Date: Jan. 6, 2020

(87) PCT Pub. No.: WO2019/010462
PCT Pub. Date: Jan. 10, 2019

(65) Prior Publication Data
US 2020/0143195 A1     May 7, 2020

Related U.S. Application Data

(60) Provisional application No. 62/529,397, filed on Jul. 6, 2017.

(51) Int. Cl.
    *G06Q 10/00*        (2023.01)
    *G06F 18/22*        (2023.01)
    *G06Q 10/08*        (2023.01)
    *G16H 40/20*        (2018.01)

(52) U.S. Cl.
CPC ............. *G06Q 10/08* (2013.01); *G06F 18/22* (2023.01); *G16H 40/20* (2018.01); *G06V 2201/034* (2022.01)

(58) Field of Classification Search
CPC ................. G06K 9/6201; G06V 10/10; G06V 2201/034; G16H 40/20; A61B 90/96; G06Q 10/08
See application file for complete search history.

(56) References Cited

U.S. PATENT DOCUMENTS

2009/0317002 A1* 12/2009 Dein ...................... A61B 50/20
                                                  340/568.1
2011/0005342 A1* 1/2011 Treat ...................... G16H 40/40
                                                  414/754

(Continued)

*Primary Examiner* — Md K Talukder
(74) *Attorney, Agent, or Firm* — Thomas J. Osborne, Jr.; FisherBroyles, LLP

(57) ABSTRACT

The instant disclosure relates to camera-based and image-based methods and systems for accurately and efficiently assembling and completing stocked or arranged disparate-shaped components of a collection using electronic images for identification. In one implementation, for example, methods and system are provided for accurately and efficiently assembling and assisting assembly of and completing stocked and/or arranged surgical instrument trays. These services are, for the most part, provided by Sterile Processing Departments (SPD) of any hospital or surgical center. SPD service facilities are common to hospital and surgery centers throughout the world.

18 Claims, 11 Drawing Sheets

(56) References Cited

U.S. PATENT DOCUMENTS

| | | | |
|---|---|---|---|
| 2013/0066647 A1* | 3/2013 | Andrie | G16H 20/40 |
| | | | 705/2 |
| 2013/0163831 A1* | 6/2013 | Tanaka | G06V 40/161 |
| | | | 382/118 |
| 2014/0288952 A1* | 9/2014 | Smith | G06Q 40/08 |
| | | | 705/2 |
| 2015/0224650 A1* | 8/2015 | Xu | B25J 9/1692 |
| | | | 414/730 |
| 2018/0247711 A1* | 8/2018 | Terry | A61B 50/18 |
| 2020/0143195 A1* | 5/2020 | Montano | G06Q 10/08 |

* cited by examiner

METHOD AND SYSTEM FOR ASSEMBLING AND COMPLETING A COLLECTION OF INDIVIDUAL DISPARATE-SHAPED COMPONENTS WITH IDENTIFICATION VIA ELECTRONIC IMAGES

CROSS-REFERENCE TO RELATED APPLICATIONS

This application claims the benefit of U.S. provisional application No. 62/529,397, filed 6 Jul. 2017, which is hereby incorporated by reference as though fully set forth herein.

BACKGROUND a. Field

The instant disclosure relates to methods and systems for accurately and efficiently assembling and completing stocked or arranged disparate-shaped components of a collection using electronic images for identification.

b. Background

In a typical hospital environment, used, non-sterile instruments are collected after being used and are placed in a container dedicated to hold non-sterile instruments. The instruments are cleaned, inspected, identified, placed into specific trays and sterilized for use in specific applications or procedures by a Sterile Processing Department (SPD) of a hospital or surgical center. The instruments may, for example, include surgical instruments or examination instruments that may be used in surgical or examination procedures within the hospital or surgical center.

The instruments are currently typically manually sorted by the SPD services by one or more users into specific instrument collections, such as surgical instrument packs, that may be specifically sorted for one or more predetermined procedures. Errors in the sorting process, whether by misidentification, counting or other error, may result in a delayed procedure while the correct instrument is found and may require opening a completely separate collection of instruments. Once a collection is opened, whether one or all of the instruments are actually used, each item in the collection needs to be recollected, cleaned, inspected, identified, re-sorted and re-sterilized into specific trays before being used in a new procedure.

BRIEF SUMMARY

Various example implementations provided relate to camera-based and image-based methods and systems for accurately and efficiently assembling computer-assisted assembling and completing stocked or arranged disparate-shaped components of a collection using electronic images for identification. In one implementation, for example, methods and system are provided for accurately and efficiently assembling and completing stocked and/or arranged surgical instrument trays. These services are, for the most part, provided by Sterile Processing Departments (SPD) of any hospital or surgical center. SPD service facilities are common to hospital and surgery centers throughout the world.

Although medical applications, such as surgical and examination applications, are discussed in detail herein, other instrument uses are similarly contemplated. For example, a camera-based method or system for assembling and completing a collection of individual components with identification via electronic images may include virtually any type of component or collection. For example, other components and collections may include, but are not limited to food supply services; maintenance services; off-shore platforms, wind farms, military ordinance facilities, sound and video systems services; disaster emergency service providers; pipe organ service providers; medical service areas in MASH units or on board Naval vessels.

In one implementation, for example, methods and systems are provided to take used and contaminated surgical instruments that emanate from an operating room (OR), separate and decontaminate and inspect the individual instruments, place the instruments on a conveyor line which will then allow each individual instrument to be identified and "entered" into the system's processing capabilities. The methods and systems can rely on images compiled and stored in the system to identify each instrument used in a given location (e.g., a hospital). The stored information, for example, may comprise one or more images that may be used manually or automatically (e.g., automated image recognition software) to identify one or more instruments for selection in a collection. The methods and systems can then determine whether the particular identified instrument is required to be included in a particular tray. In one implementation, for example, the methods and systems may include one or more target and/or required time period in which the user should identify the correct instrument for placement in the collection. The content of a particular collection (e.g., a surgical instrument tray) that has been determined by the hospital's practices and the identity of the tray and its contents will be an established fact. In various implementations, for example, a hospital or surgical center has a roster of identified trays which are an established part of that institution's modus operandi. The sterile processing department (SPD) of a hospital can know what instruments are to be included in a particular collection (e.g., tray) and the identity of each instrument and tray may be particular to that institution's nomenclature. Further, there is likely more than one exclusive fabricator of a given instrument. The selection of a given instrument might be very particular to the team or surgeon that requisitions the instruments they are expecting to use in a procedure. In many instances, surgeons will only use instruments fabricated by a very specific manufacturer.

The methods and systems can use a stream of individual instruments to compile individual trays which have been given a "due for use" timestamp by the OR schedules sent to the SPD for processing. The methods and systems can respond to the instructions sent to SPD to allocate instruments being processed or held in inventory, to compile the contents of individual trays. The methods and systems can also have the capability of responding to changes in priority for trays. Once a tray is completed, it can be passed on to a sterile processing station where the tray is reviewed by an operative of that station, corrections or missing instruments included and the completed tray is then appropriately sealed, properly identified and subjected to a sterilization process. The operatives of the sterilization station may also have an identification system available to them to be able to confirm the required contents of a particular tray that they are working on so that they can confirm that a tray is indeed complete. In some implementations, every hospital or surgical center can have an independent, established way in which a completed tray is identified and its contents acknowledged. Also, every hospital or surgical center can have an established way in which a completed tray is placed directly onto a cart or stored for inclusion on a cart destined for an OR.

The foregoing and other aspects, features, details, utilities, and advantages of the present invention will be apparent from reading the following description and claims, and from reviewing the accompanying drawings.

DETAILED DESCRIPTION

Figure 1:
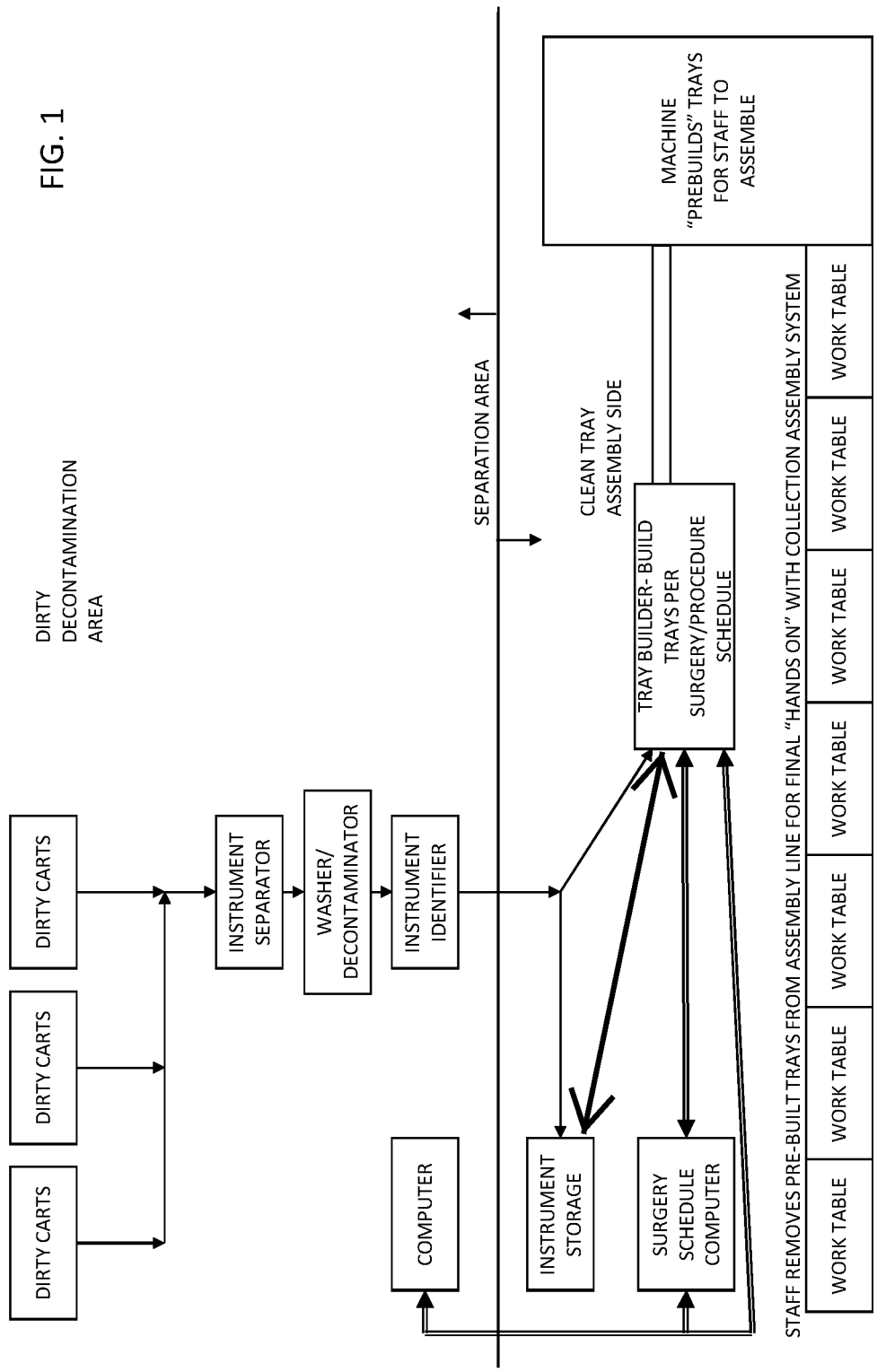
FIG. 1 shows an example implementation of a method and system for accurately and efficiently assembling and completing stocked or arranged components of a collection.

FIG. 1 shows an example implementation of a method and system for accurately and efficiently assembling and completing stocked or arranged components of a collection. In one implementation, for example, methods and system are provided for accurately and efficiently assembling and completing stocked and/or arranged surgical instrument trays for use in one or more surgical procedures. In this example implementation, one or more carts (or other receptacles) of used, dirty or contaminated instruments are received in a decontamination area. The carts, for example, may be pre-sorted by type, use or other category and received for decontamination. In other implementations such as shown in FIG. 1, for example, an instrument separator (manual and/or automated) provides a pre-sorting operation, such as sorting the instruments by general category, use or other method. The sorting method, for example, may include separating the instruments by use or category of instrument and may be placed in groups in containers, on hooks, or the like for initial cleaning and performance inspection.

In this implementation, the pre-sorted (or non-sorted) instruments are then received at a washer/decontamination station in SPD where the instruments are cleaned and readied for selection.

The cleaned/decontaminated instruments are then received at an instrument identification station in the SPD. The instrument identification station, for example, may include a manual and/or automated identification procedure such as described in more detail herein.

In one implementation, for example, the instruments are inspected by a sorter that compares the appearance to one or more images. The images, for example, may be preselected by a person or the system (e.g., a software program of the system) to aide in identification of the instruments. The images, for example, may be pre-selected to visually show one or more characteristics of the instruments to aid in identification or selection of a particular instrument. The inspection may be by a user comparing the instrument to the one or more images and/or by an automated image recognition system in which an image taken by a camera is compared to the one or more preselected images. The preselected images, for example, may include an image of the overall instrument and/or images (e.g., close up images) of portions of the instruments that are predetermined to aide in rapid and correct identification, whether by a user and/or an automated image recognition system.

As shown in FIG. 1, for example, a computer system may include software, hardware and/or firmware for aiding the instrument identification.

From the instrument identification station, instruments may be passed from a dirty/decontamination side to a clean assembly side, although in other implementations, the designation of the dirty decontamination and clean assembly sides may include other combination of stations such as but not limited to the instrument identification station being on either side of the system.

The clean assembly side, shown in FIG. 1, for example, may include instrument receiving stations for storage (e.g., instruments not immediately needed to build one or more collections) or a collection builder (e.g., tray builder) for use in building one or more collections as needed for use or storage.

A collection scheduler computing system (e.g., surgical scheduler computing system) may be used to identify one or more collections of instruments for each scheduled event (e.g., surgical procedure) and provide one or more list of items to be placed in each collection. The lists of items for each identified collection are provided to the collection builder station in SPD for use in selecting items for inclusion in each collection to be built.

Individual collections (e.g., surgical trays) are built/assembled at an assembly station in SPD. The assembly station may further include inspecting instruments by a sorter that compares the appearance to one or more preselected images that are selected to aide in identification of the instruments, such as described with respect to the instrument identifier station. As described above, the inspection may be performed by a user comparing the instrument to the one or more images and/or by an automated image recognition system in which an image taken by a suitable compatible camera is compared to the one or more preselected images. The preselected images, for example, may include an image of the overall instrument and/or images (e.g., close up images) of portions of the instruments that are predetermined to aide in rapid and correct identification, whether by a user and/or an automated image recognition system. Where the instrument identification is done at the assembly station in the SPD, for example, the instrument identifier may be a rough or pre-sort process that groups instruments, such as by use or category for specific identification at the collection assembly station. As shown in FIG. 1, for example, a computer system located at the assembly station, the surgery scheduler computer and/or the instrument identification computer may include software, hardware and/or firmware for aiding the instrument identification.

The clean assembly side identified in FIG. 1, in this particular implementation, further includes one or more work tables that may be used for final handling of the assembled collections (e.g., surgical trays), such as Prostate Extraction or treatment, Abdominal Hysterectomy, Vascular Triple Bypass, Hip Joint Replacement, Ankle Reconstruction etc.

In one particular implementation, for example, the identification methods and systems may analyze each instrument being identified via three-dimensional (3D) analysis. For example, each instrument may be hung by hooks, placed on flat surface, or placed in a location (e.g., a trough) by trained staff or robotic system for 3D recognition and identification within the system. In this implementation, this could take place in the instrument separator station, the instrument identifier station and/or the collection builder station, all currently located in SPD. Each instrument, for example, may be subjected to imaging by a plurality of cameras and/or angles for identification purposes. In one implementation, for example, software instrument identification may be performed in approximately one instrument per second. The 3D system may, for example, take images of instruments, identify instruments and determine the next case placement in the instrument identifier or collection builder station. If one or more particular instruments are not needed for a currently scheduled collection, the instruments may be moved to the storage station for later use.

Instruments sent to the storage station may, for example, be catalogued (e.g., in a data base or other data storage) and retrieved as needed for collections scheduled to be assembled as they are received or scheduled for assembly. Hardware, software and/or firmware may be connected to one or more computer system, such as the example systems shown in FIG. 1.

Instruments may be placed in "storage or inventory" in any number of manners. The instruments, for example, may be stored by individual device or category of device in specific locations (e.g., bins) or the locations of the individual instruments may be identified by label or by data structure within one or more of the computing systems. The instruments may be stored manually and/or automated (e.g., via one or more robotic system that may also be able to find and/or retrieve the instruments from storage). Hardware, software and/or firmware may prepare next use collection (trays) builds, such as by OR schedule. These builds may be from the storage instrument inventory and/or from the instruments received directly from the instrument identifier station. The collections (e.g., surgical instrument trays) can be bar coded, labeled with identifying information (e.g., case, doctor, date, OR room, time of assembly, etc.), assigned an RFID or any other identifier.

In one implementation, for example, instruments needed within a particular time period (e.g., 48 hours) can be built into requested trays for sterilization at the need of the surgery schedule or requisitions. Software, for example, can make a determination on build of collections (e.g., trays) at any time based on an inventory of instrumentation and known schedule or "assumption of schedule" which can be determined by an algorithm of a particular facility's routines.

As described herein, instruments not requested for use can be moved to clean or sterile storage and software can regulate the storage. These instruments, for example, can be moved by conveyor and placed into holding containers. They can be "retrieved" as needed by software, hardware and firmware that can, for example, open container doors automatically when staff presents preprinted ticket to bar code system. Staff receives "built" trays for from clean side machine and completes process from work tables for surgical needs. The staff member picks up the built trays from conveyor belt coming out at "tray builder machine" on clean side.

In some implementations, software can update needed trays and held storage inventory every time a new case is scheduled from an OR, every 30 minutes, and uses prior "Case load possibilities". In other words the system can be "smart" and pick up tendencies in doctor uses, doctors block times, Friday Night Traumas, Births, etc. Machine learning and/or artificial intelligence (AI) techniques may be utilized to adjust schedules, collections, components or the like, such as by anticipating current or future workflow based on past experience/patterns. Software may also know what to hold (e.g., in storage), what and when to build, and build from complete inventory being used in real time and stored inventory.

Trays that go to surgery and come back unused from cancelled cases are bar coded back into system. The system can identify the contents of the tray and determine whether the content is to be used for other cases, the tray is to be broken down, or whether the tray should stay assembled for use based on a schedule (e.g., a 48 hour awareness schedule) and may be given a new bar code or other identifier or the current identifier status updated in a tracking system.

Each identified instrument in the system can correspond to one or more recorded data points. Every action taken by the software can be recorded and timestamped as a source of pertinent data for the purposes of quality assurance and control. Specifically, these data can be used to perform root cause analyses (i.e., tracking of problems) as well as to create statistical benchmarks of time, error rates, peak usage, etc. for the purposes of workflow evaluation (of workers, SPD units, hospitals, particular days and particular times of days, particular types of operations, etc.). In one example, a system can collect, store, process and use information learned from one location across a market. For example, a formula to cost new tray use/surgeons/specialties for facilities through an algorithm may be used for workflow benchmarking as a reliable source of baselines for statistical evaluation.

In another implementation, a system may identify instrumentation, such as through 3D recognition, at a point of decontamination utilizing instrumentation for a plurality of case load procedures. In this example, instruments can be assigned to any tray that requires that particular instrument. Instruments need not be exclusively assigned to a particular collection or tray. The system, for example, may provide for elimination asset storage, increase in productivity (e.g., by 90%) of instrument identification. Hardware may include, by way of example, a 3D module, robotics, conveyor belts, a storage machine, and data storage to use the process software and store data.

In one implementation, for example, a collection (e.g., an encyclopedia) of photographic images is stored electronically and those images are used as references when a camera has an actual instrument used in a surgical process, or an article used in the process of sterilizing the contents of a surgical tray of instruments, placed in view of the lens of the camera and the system is able, with a degree of accuracy, to identify the instrument or article, such as through pattern recognition.

In one implementation, the methods and systems may be concentrated in the area of a hospital that is known as the SPD (Sterile Processing Department) and in other areas of a hospital or a surgical center as well as such locations are the anti rooms to an operating theatre—i.e. locations where reviews of carts and their contents might be subjected to audits or procedural reviews and where the ability to be able to identify individual instruments, or confirm the content of sealed trays, is of importance. However, it should be recognized that the concept can be used in a great number of applications that are not limited to the confines of a surgery, and operating theatre or a hospital's facilities. There are many other situations where the need to accurately identify objects accurately and the use of an image storage facility is the most accurate and reliable means by which that identification can take place. For example, Pharmaceutical, Mechanical, Engineering, Military and/or any other process where human interaction and objectivity might be used for distinct pattern recognition and decision making.

In one particular implementation, for example, a system includes one or more computerized/automated systems having one or more of the following uses:

Software/hardware used to assist in the process of selecting the instruments that are called for by a surgeon of a surgical team to enact a specific or a defined surgical procedure. The system can receive a requisition of instruments and supporting items, such as temperature indicators, masks, pads, etc. and the individual items will be selected by the operative and all the defined or identified instruments and items will be included in a particular collection (e.g., tray) for the tray to be considered complete.

The system is configured to ensure that contents of a given collection (e.g., surgical tray of instruments) are accurately selected; that any deviations from the required list are noted and recorded; that the time taken to pack the given tray is recorded; that the person or persons involved in the compilation of the tray are recorded; that a record is made of the content of that particular tray so that the way in which individual instruments are used in a surgical procedure can be accurately identified as to the multiple procedures that a given instrument can be used for. These data would be valuable for conducting root cause analyses, when appropriate. The system can also be able to identify instruments that have very limited or even exclusive uses assigned to them. Data collection can be specifically tailored for statistical analysis for the purposes of evaluating a given facility using the inventory of instruments.

The system can allow an area manager to identify where problems in the process are occurring. The system can also provide reliable data on why there is an excellence in the functioning of a given area and help to demonstrate the component parts of a notably successful area's outcomes.

In one implementation, the system can be used for employee training, testing/evaluation, or as a refresher course. For example, staff that appear to be making identification mistakes on recognizing instruments, or responding to changes in a surgical procedure that now requires that different instruments, or more instruments be available at the time of the operation, can be walked through the assembly process using instruments that are not taken out of the line of instruments, required to be available for an up and coming procedure. Similarly, a person that has no experience in the very exacting procedures of selecting very specific instruments that are to be included in a given surgical instrument tray, can be allowed to learn how to pack a tray, using the images set before them and learning how to use the images and supporting data provided to them on the system screen to accurately pack a simple or a complex tray of instruments. By using a timer discreetly noting the time that it takes an individual or individuals to identify an instrument or instruments and complete a given tray is a very important source of information to the manager as it will help them to select people that are clearly gifted to perform the functions, or help them to identify challenges that could make a person a reliable member of the tray assembly team. Additionally, the system can record, generate and provide data relating to SPD performance can also be correlated with procedure and/or patient outcomes given that there is a direct connection between the services provided by SPD and the outcome of procedures in the OR.

Because the system can be triggered by actions taken by the operator and all of the actions taken are recorded and timestamped and the system records all of these actions to each individual, identified instruments and identified trays, therefore, when the information is tabulated in a departmental experience format, the manager of an SPD is able to establish accurate, meaningful data on the costs involved in providing the tray compilation process; they are able to evaluate how staff perform in this specific function; how many problems with missing or non-functioning instruments are being experienced; how well new staff are learning and responding to the process of accurately packing instrument trays; accurately informing the manager of which individuals are able to consistently pack trays accurately and in a timely way; how many instruments in the inventory of a hospital have multiple uses and how many have exclusive uses. With better procedures, the use of multiple use instruments could notably reduce the need for excessive inventory items.

Where a tray requisition cannot be closed until every item on the list has been addressed, once the tray is released to the sterilization process, a printout report can accompany the tray and clearly set out if there are instruments missing or substituted—and what steps have been taken to correct this situation or set out what decision maker has been consulted to allow for the exception or a substitution. By the time the tray reaches the operating theatre, the support staff will be able to look at the individual tray's report and see if it is 100% as required or if there are exceptions, exactly why the exception has been authorized and who authorized the exception.

In one particular implementation of an SPD installation, a system can include one or more "master" unit (e.g., computer/tablet) for each SPD in which is housed a complete roster of all the instruments that that a particular hospital or surgical center uses. The master unit, for example, could be the only unit that was able to share information with either carefully screed staff members of the hospital and it would be the master that would regularly communicate with a centralized office with respect to information gathered, changes in instrument images, changes in the make-up of a given tray, changes in data gathering, changes in makeup of a tray for an identified surgical procedure, changes in the routines of a hospital that effect the services required of the SPD in regards to the availability of sterilized surgical instruments, or the like.

From the master unit, up to a given number of satellite units (e.g., tablets) that are linked to the master, likely by a simple blue-tooth or other wireless or wired connection, and be placed in the same SPD area. In one implementation, for example, each tablet may be self-contained and that is a system by which, on a regular basis, the information contained in that satellite unit is downloaded to the master which then communicates the compilation of information to a centralized controller. Further, in one implementation, each system installed in a given SPD may be self-contained and not remotely rely on an active connection (e.g., WIFI or cable link) to the centralized system. On a regular and controlled basis, the master can send information to the service provider where such things as billable units will be calculated and performance experiences can be tabulated and compiled, where images with all supporting information will be compiled etc.

A master unit can control such things as password authority for personnel to access the system. The master unit can also hold the authority of approved personnel to in any way add or subtract information for the given system. The master unit of one or more particular facility may or may not be able to access a centralized system maintained by a service provider. Thus, a given client may or may not use the system to obtain any information from the service provider.

As images of the instruments used in a given facility are amassed, a system can include two or more image banks or collections. In one example system, instruments that are used by a particular facility, irrespective of whether it is an individual non-affiliated facility or a part of a multi-facility ownership group, can be kept in a clearly identified file which only records the instruments used by that particular facility and also, specifically identifies the nomenclature and content of a specific tray that is used at that particular facility.

A centralized data bank can also keep a record of each instrument that any hospital or surgical facility, which is a client, in a form that identifies that particular instrument with any given name that is associated with that particular instrument. The use of that particular instrument, whether in multiple applications or very specific uses can be recorded. Where a particular instrument is fabricated by more than one manufacturer that can also be noted. Where substitutions have been authorized, those incidents can be recorded along with the identity of the substitution instrument. The centralized data bank can also keep a list of the name of the fabricators of specific instruments and the number of client facilities that are using those specific instruments.

A cross referencing data bank can allow a client to be able to find alternate suppliers of a given instrument or find instances of where different instruments have been used in a given tray than those that happen to make up their trays contents. In various implementations, facility specific data (e.g., how a facility is using an instrument or combination of instruments) can be restricted from access by other facilities depending on confidentiality concerns.

The data bank can also keep data that allow a centralized system to establish meaningful records of the time that trays typically take to be compiled; the results of spot audits that confirm the accuracy of those that are using the system to make up their collections/trays; the time that it takes to train skilled operative as opposed to persons that are completely new to the process. The reasons for errors that are identified by audits can be recorded with password protection as to the specific facilities that experienced error situations that occurred—particularly when the system was being used. The capability of the system will also allow administrators and managers to see if there are a combination of identifiable characteristics in personnel and context (SPD unit, time of day and day of the week, type of surgery, etc.) that tend to produce the most reliable and effective members of the SPD team (or most problematic).

The use of all or part of the image data can also be used by the software system that can be used in a mechanical/manual, semi-automated or automated process by which instruments can be accepted directly from an operating theatre and then process the instruments using specialized equipment where required, to ultimately pack the trays of instruments with the contents being in conformity with the requisitions given to the SPD area for up and coming surgical procedures.

In some implementations, the system can use image software to identify individual instruments and as the instruments flow through the system, those electronic images will then allow robotic systems to pack the individual instrument trays and present the trays to the operatives of the final sealing procedure and sterilization process. It should be noted that the system, in some implementations, can process instruments that are taken to the point where they are considered clean, but not sterilized. While in other implementations, sterile operating conditions may allow an automated system to process even sterilized instruments.

In one example implementation, a system may allow an SPD to greatly improve the outcome of accurately packed and prioritized surgical instrument trays. A hospital that uses part or all of the system, for example, could have only a small area dedicated to the compilation of surgical instrument trays and the personnel requirements of the SPD for this particular function could be substantially reduced. Further, the cost of training new operatives would be substantially reduced and be easily monitored and proficiency would be easily recorded.

In some implementations, a system may provide for a person to place an instrument under an electronic camera, and for the camera to consult a library of images of instruments that are associated with that particular facility and identify the instrument to the person. A "station" can include a camera on a suitable stand; a pad that has clear, scaled squares printed on the surface so that the size and relevant scale of an instrument is clearly evident to the lens of the camera. In this particular implementation, for example, the system may be geared to instruments of a maximum size. The unit, for example, may be in an SPD area; possibly in a sterilization station; be present on a special cart that is present in an operating theater close to where trays are unpacked and the instruments laid out on a surface for the support staff to hand to a surgeon or to an actively involved support staff member. The facility could include of a fully "loaded" unit (e.g., a tablet that holds a record of all the images associated with that particular hospital) and the camera and a scaled surface. (It is likely that the camera and the tablet would be in an enclosure that would negate the need for having the camera and the tablet surfaces to be sterilized or subjected to sterilization processes. Only the scaled platform may need to be subjected to sterilization of surfaces procedures.

In yet another implementation, a system can be configured to allow a person to access a cart on which the sterile and sealed trays of instruments are placed awaiting being moved into an operating theater. A person, with a barcode reader could select any tray, read the barcode and the person could then "ask" a unit (e.g., a master unit) to identify the contents of that particular tray. For example, any tray that has been packed and against which there is an "open" barcode can be scanned for its content. As a sealed tray is opened, the particular tray's barcode can be cancelled as a part of the post-operation routine. If a tray is not opened but is transferred to a "new" cart, the barcoded tray can be entered into the system as a completed tray—and perhaps a new barcode attached to/associated with it indicating that it was a previously compiled, complete and sterilized tray.

In another implementation, in a given hospital, a tablet or other unit of a system can hold a complete set of instruments used in that particular hospital or facility so that an authorized person can access the tablet and ask it to identify by name or by image, any instrument and all its relevant information so that a person could familiarize themselves with the characteristics of that particular instrument. On the same tablet, there can be a complete list of all the trays that the particular hospital typically uses and the contents of the trays will be set out. The procedures that typically use a given tray can also be identified. The information held in a hospital-specific unit can be compiled by authorized personnel in that particular facility.

A unit that is supplied to an institution that teaches people to become a member of the medical world—doctors, surgeons, nurses, etc.—at the school or university where the skills are being taught, can be used to supply that institution with one or more fully programmed tablet or tablets which will contain images taken from the central information bank that will identify any instrument that the centralized client roster is using. The instrument can be identified; all supporting information about the instrument can be available; typically what procedures this instrument is used at, etc. However, where confidential, the identity of a particular entity or the association of a particular instrument or group of instruments may be kept confidential. The system can also provide an option that includes a camera ID facility attached to the system so that a student or teacher can place the instrument under a lens and have the instrument identified by the unit.

A GLOBAL system can be provided by which a client in any part of the world access a suitable programmed and updated GLOBAL unit that can identify any instrument that is used by any client in any part of the world with its attendant images and data attached to that image. The GLOBAL unit can also be able to identify any given instrument by name, reference number. A cross-reference system could be a part of the service offered. One particular feature of this service could enable a person to establish a situation where EXACT substitutions, identified by different manufacturers or other known instrument code numbers, etc., could take place.

It is of note that the systems described have many other medical or non-medical applications for the concept set out by the systems described herein and it various derivations. For example, the use of images, with the attendant ability to harvest statistical data, human factors data, such as personnel traits, usage patterns, along with compilation of instruments or given products (such as pills or medications for instance or tools that are used to service machines or complex computer systems, service complex industrial machines or military equipment), etc.

The images on display screen shown herein, in some implementations, may be zoomed in, zoomed out, moved within an image location of the GUI to enable closer inspection of the stored image and comparison of the image to an actual device being analyzed. The GUI also includes Row Up, Row Down, Page Up and Page Down icons for navigating within a list of related instruments. Further, other icons include Count Complete, Pause Count, Cancel Count and Quick Turnaround. The Count Complete, for example, may be selected when a particular instrument is identified and selected for a collection and/or a proper number of the particular instruments are identified and selected for a collection. The Pause Count icon may be selected when a timer for the collection is to be paused (e.g., for a break, to retrieve more instruments for processing, etc.). The Cancel Count may be selected, for example to cancel looking for a particular instrument and/or to cancel counting where an instrument is not actually found (e.g., the instrument in hand does not match the stored image shown). The Quick Turnaround icon may be selected when a collection of instruments is identified as needed in a critical "time stamp" situation that is different from the 48 hr awareness schedule. Of course, these particular icons are merely examples and other ideas (such as touchscreen, scrolling, etc. are also contemplated).

The automated or assisted image identification system may also allow for removing identification labels used in many hospital environments that have been known to be damaged over time, such as by cracking and potentially peeling. By eliminating such labels, particles from those labels may be eliminated and thus reduce foreign matter being introduced during a surgical procedure.

Figure 2:
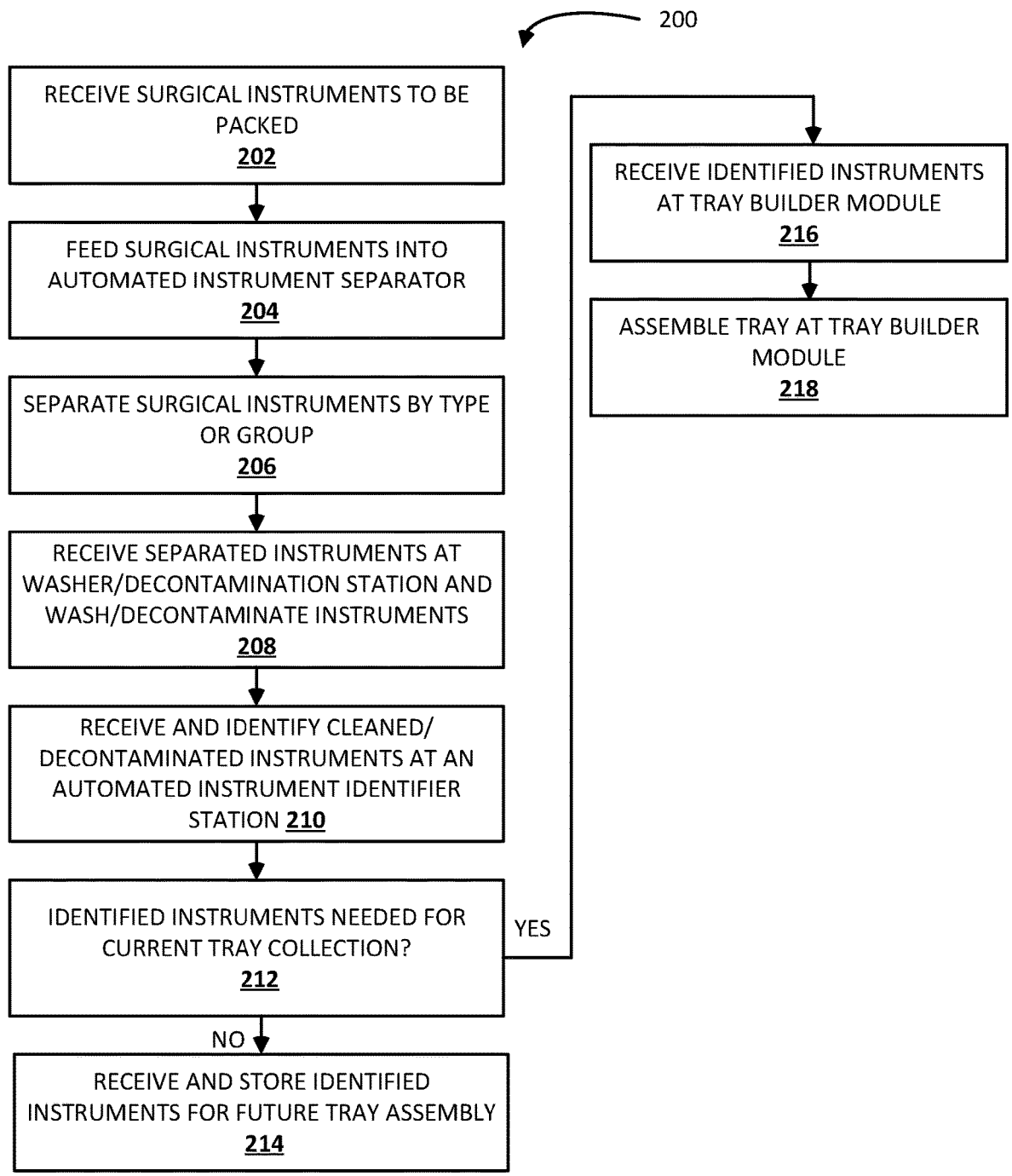
FIG. 2 shows a flowchart depicting an example generally automated process of identifying and assembling a collection of disparate components.

FIG. 2 shows a flowchart depicting an example generally automated process of identifying and assembling a collection of disparate components 200. In the process shown in FIG. 2, for example, a generally automated surgical tray assembly process is shown by way of example. One or more carts including used or dated surgical trays are received in an operation 202. The surgical trays, for example, may include a plurality of surgical instruments received at an SPD of a hospital to be cleaned and reassembled in one or more new surgical trays. In this example, the surgical instruments can be fed into an automated instrument separator in operation 204 and separated in operation 206. The instruments may, for example, be received via a conveyer belt, bins, hooks, robotics or other instrument handling devices that allow for the instruments to be received and separated from each other. The separated instruments are then fed into one or more washer/decontamination stations in operation 208. The washer/decontamination station(s), for example, may clean the instruments to a level that is safe for handling and to prevent contaminants from interfering or building up in equipment of the system. The cleaned/decontaminated instruments are then received and identified at an automated instrument identifier station in operation 210, such as described with reference to FIG. 1. The instrument identifier system, for example, may include one or more camera elements adapted to obtain one or more image of each instrument and compare it to one or more stored image corresponding to known instruments for identification purposes. The instrument identifier system may further utilize other sensors, such as weight, dimension, size, color, material recognition or the like, to further aid identification by comparing sensor inputs to stored data related to known instruments. For example, where similarly shaped instruments vary by weight, mass, material, dimension or the like, the automated system may compare information captured by the sensors to stored data of known instruments. Further, in various implementations, the instrument identifier may obtain definitive identifications of each instrument or classify instruments according to two or more groups of related instruments that can be further distinguished in one or more additional steps.

Once identified (individually or according to groups), the instruments may be fed to storage or to a tray builder process (e.g., an actively processing tray builder process) to be assembled into one or more surgical trays for use within a predetermined time period (e.g., 48 hours). Where the instrument(s) are not listed as components for particular predetermined surgical tray collections being actively assembled or scheduled for near-term assembly in decision operation 212, the instruments may be fed (e.g., via one or more conveyor, bin, hook, robotics or other instrument handling devices) to an instrument storage where the surgical instrument(s) is identified and stored for later retrieval in operation 214. Where the instrument(s) are identified as components for particular predetermined surgical tray collections being actively assembled or scheduled for near-term assembly in decision operation 212, the instruments may be fed (e.g., via one or more conveyor, bin, hook, robotics or other instrument handling devices) to a tray builder module in operation 216 that assembles one or more surgical tray collections by matching the identified surgical instruments with predefined components of a surgical instrument collection to be assembled (e.g., via a surgery schedule computer such as shown in FIG. 1) in operation 218. The tray builder module, for example, may include one or more instrument handling device, such as conveyors, sorters, bins, hooks, robotics or other instrument handling devices, for handling the instruments and assigning/placing the surgical in one or more surgical trays based on the assembly lists of components (e.g., stored on a computer system such as the surgery schedule computer shown in FIG. 1). The tray builder module may receive surgical instruments directly from the instrument identifier (or other component described herein) and/or from instrument storage.

In this particular example implementation, the tray builder or a downstream packaging module finalizes the assembled surgical instrument tray collection, labels or otherwise identifies the assembled tray (e.g., barcode, RFID, label, code or the like) for later identification. The assembled tray can then be sterilized and stored for an upcoming surgery, whether scheduled or likely to be needed based on history.

Figure 3:
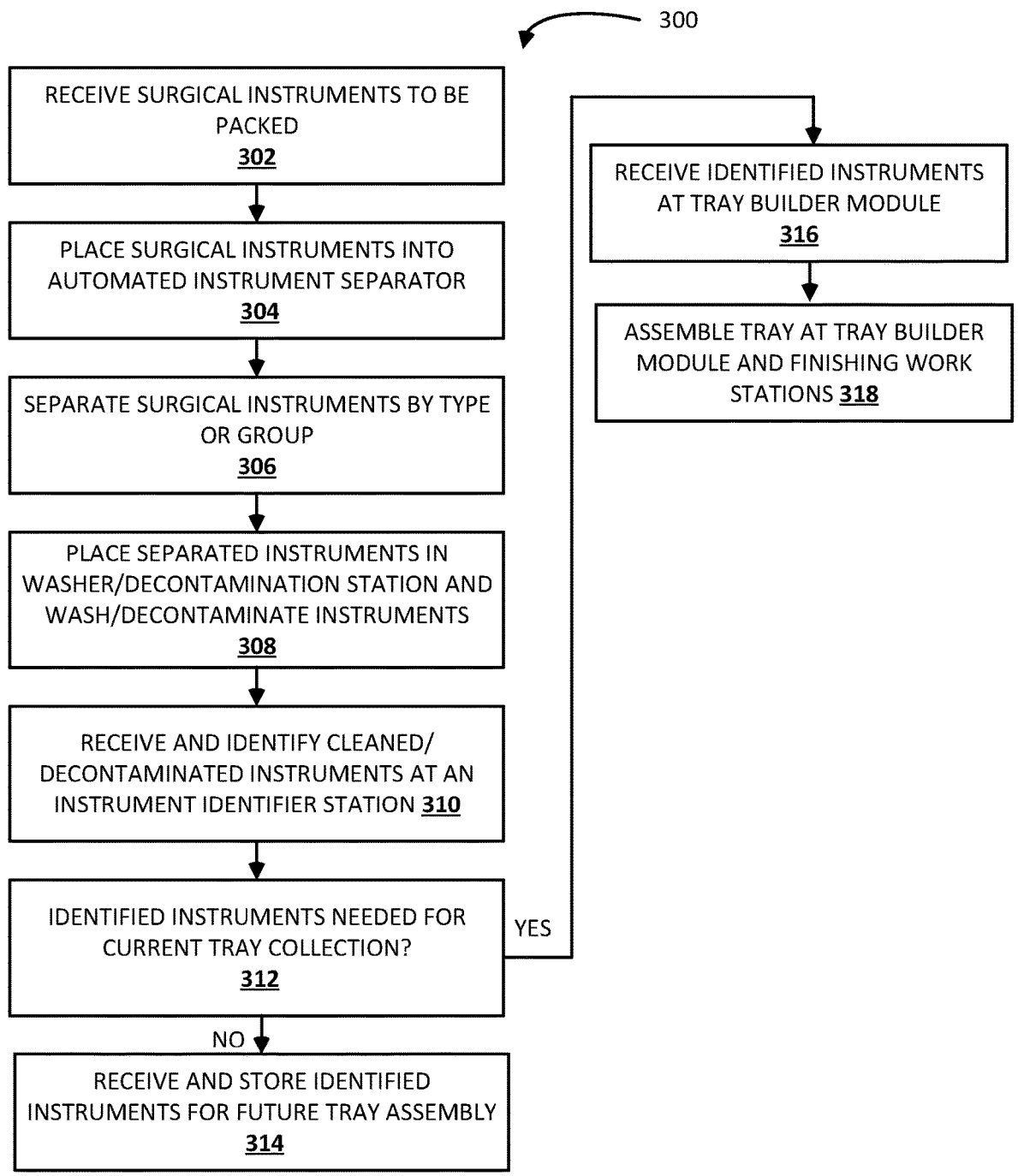
FIG. 3 shows a flowchart of another example process of identifying and assembling a collection of disparate components 300 in which one or more operations include generally manual/computer assisted operations

FIG. 3 shows a flowchart of another example process of identifying and assembling a collection of disparate components 300 in which one or more operations include generally manual/computer assisted operations. In the process shown in FIG. 3, for example, a generally manual/computer assisted surgical tray assembly process is shown by way of example. One or more carts including used or dated surgical trays are received in an operation 302. The surgical trays, for example, may include a plurality of surgical instruments received at an SPD of a hospital to be cleaned and reassembled in one or more new surgical trays. In this example, the surgical instruments can be manually received on one or more carts and placed into an instrument separator station in operation 304 where the instruments are separated by one or more attendants, such as by instrument type or grouping in operation 306. The separated instruments are then fed into one or more washer/decontamination stations in operation 308. The washer/decontamination station(s), for example, may clean the instruments to a level that is safe for handling and to prevent contaminants from interfering or building up in equipment of the system. The cleaned/decontaminated instruments are then received at instrument identifier station in operation 310, such as described with reference to FIG. 1. The instrument identifier system, for example, may include one or more workstations, such as described with reference to FIGS. 4-10 herein, that assist a user to identify the instruments. The workstations, for example, may include one or more computers or monitors that show image(s) of one or more distinguishing features of the instruments to assist the user in identifying individual or groups of common instruments. The workstations may further utilize camera(s) and/or other sensors, such as weight, dimension, size, color, material recognition or the like, to further aid identification by comparing sensor inputs to stored data related to known instruments. For example, where similarly shaped instruments vary by weight, mass, material, dimension or the like, the automated system may compare information captured by the sensors to stored data of known instruments. Further, in various implementations, the instrument identifier may assist a user to obtain definitive identifications of each instrument or classify instruments according to two or more groups of related instruments that can be further distinguished in one or more additional steps.

Once identified (individually or according to groups), the instruments may be fed to storage in operation 314 or to a tray builder process in operation 316 (e.g., an actively processing tray builder process) to be assembled into one or more surgical trays for use within a predetermined time period (e.g., 48 hours) depending on the outcome of decision operation 312. Where the instrument(s) are not listed as components for particular predetermined surgical tray collections being actively assembled or scheduled for near-term assembly in decision operation 312, the instruments may be provided (e.g., manually or via one or more conveyor, bin, hook, robotics or other instrument handling devices) to an instrument storage where the surgical instrument(s) is identified and stored for later retrieval. Where the instrument(s) are identified as components for particular predetermined surgical tray collections being actively assembled or scheduled for near-term assembly, the instruments may be provided (e.g., manually and/or via one or more conveyor, bin, hook, robotics or other instrument handling devices) to a tray builder module that assembles or assists one or more users to assemble one or more surgical tray collections by matching the identified surgical instruments with predefined components of a surgical instrument collection to be assembled (e.g., via a surgery schedule computer such as shown in FIG. 1). The tray builder module, for example, may include one or more workstation such as described with reference to the instrument identifier to assist the user in assembling (or pre-assembling) the one or more surgical tray collections, such as described in more detail with reference to FIGS. 4-10, based on the assembly lists of components (e.g., stored on a computer system such as the surgery schedule computer shown in FIG. 1).

In this particular example implementation, the prebuilt surgical instrument tray collections may be finalized at one or more work table via a final "hands on" inspection or assembly. The completed surgical tray collections may further be finalized such as by labels or other identifiers of the assembled tray (e.g., barcode, RFID, label, code or the like) for later identification. The assembled tray can then be sterilized and stored for an upcoming surgery, whether scheduled or likely to be needed based on history.

Although the process shown in FIG. 2 is generally automated and the process shown in FIG. 3 includes generally manual operations assisted by a system, the two examples are not exclusive. Rather, operations depicted in each process may be substituted between processes. For example, one or more automated operation, such as for the instrument separator, identifier, and assembly operations shown in the process of FIG. 2, or one or more manual operation, such as for the instrument separator, identifier, and assembly operations shown in the process of FIG. 3 may be substituted for operations in a different process. Thus, the generally automated system/process shown by example in FIG. 2 may include one or more generally manual/computer assisted operations shown by way of example in FIG. 3 and the generally manual/computer assisted operations shown by example in FIG. 3 may include one or more generally automated operations shown by way of example in FIG. 2.

Figure 4:
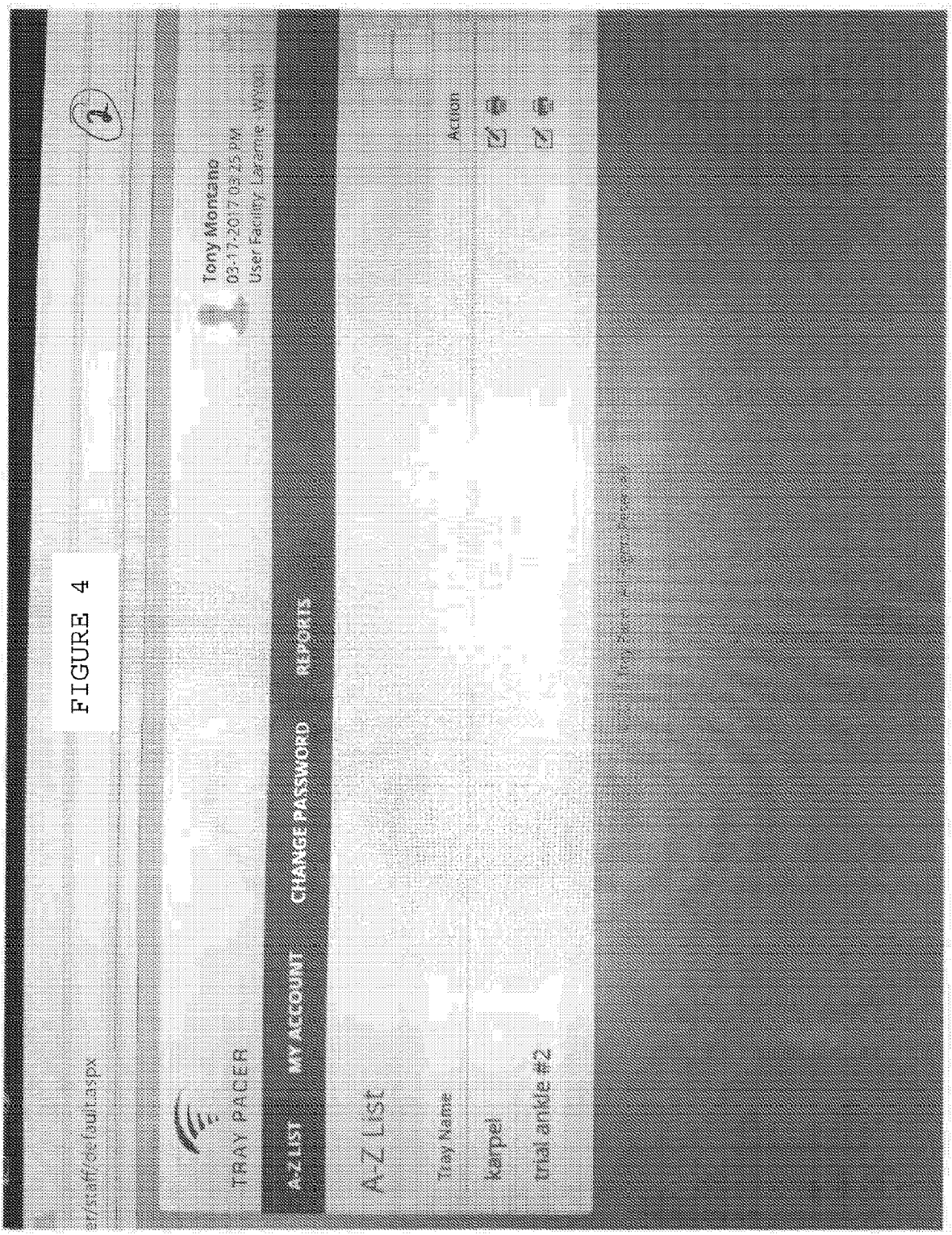
FIGS. 4-9 show example screen images/user interfaces of an example camera-based system for assembling and completing a collection of individual components with identification via one or more electronic images.

FIGS. 4-9 show example screen images/user interfaces of an example camera-based system for assembling and completing a collection of individual components with identification via one or more electronic images. In this particular implementation, FIG. 4 shows an example lists of trays (collection) of surgical instruments (components) to be assembled by a user. In this instance, the user Tony Montano is logged into the computer system and has two trays identified and/or assigned to be assembled using the system: karpel and trial ankle #2. The user can select one of the identified/assigned trays in order to start the process of assembling a tray of surgical instruments.

Figure 5:

FIG. 5 shows an example screen image/user interface for use a process of assembling a surgical tray for an example Ortho surgical procedure that has been selected and started. As can be seen in FIG. 3, the user interface shows the number of instruments to be included in the tray (16 in this example). The user interface further shows a "Tray Pacer" time that provides a target time for completing the assembly of the entire tray of instruments. The target time may be determined in any number of ways. For example, the Tray Pacer time may be a determined by a particular time per instrument and the individual time may be equally allocated or selected based on difficulty of identification and selection that may be predetermined and/or adjusted over time by reference to statistics kept by the system The system further provides an actual time on tray that displays the actual time the user has spent working on the particular tray and a total time on tray that includes off time, etc. where the user may have paused the assembly process (e.g., a break, time searching for one or more items not available at the user's station for inclusion in the tray, etc.). The system also includes a Time Differential that in this particular implementation can be used to show a percentage difference by staff performance for a particular collection and the predetermined time (e.g., benchmark, limit) for the collection so that trends, algorithms, benchmarks or the like can be determined and followed. This data, for example, may be useful immediately by the staff or supervisor and/or may be used to track historical performance after the fact.

The user interface, in this example, also shows images, icons or the like of the individual components to be included in a particular tray. In FIG. 5, for example, the user interface shows a plurality of thumbnail images on the left side of the display. The images may be scrolled through by the user and show the progress of the tray assembly. In this example, a "Goiter Green" image is shown with a time remaining indicator of "0:00" indicating that the surgical instrument was not added to the tray within the target time and the system moved to the next surgical instrument to be included in the tray, in this case an Army-Navy Retractor, Double-Ended. In this particular example, the system moves the user on to the next item in order to increase efficiency on the overall tray. The user, in various examples, may be able to override the system and continue to work on the prior instrument, or the system may return to any missed items after the remaining instruments have been identified and placed into the tray. In FIG. 3, for example, the system has moved onto the next instrument (Army-Navy Retractor, Double-Ended) and shows 00:05 seconds remaining. In some implementations, for example, the system may include various visual indicators as the timers advance past predetermined limits. For example, the thumbnail images may include indicators (e.g., colored frames) that indicate the status of progress in an easily visual clue. In one implementation, for example, frames around the thumbnail images may change colors, flash or otherwise indicate the user's current progress. The frames (or other aspects of the display), for example, may include color schemes such as green, yellow or red depending on the status.

Figure 6:
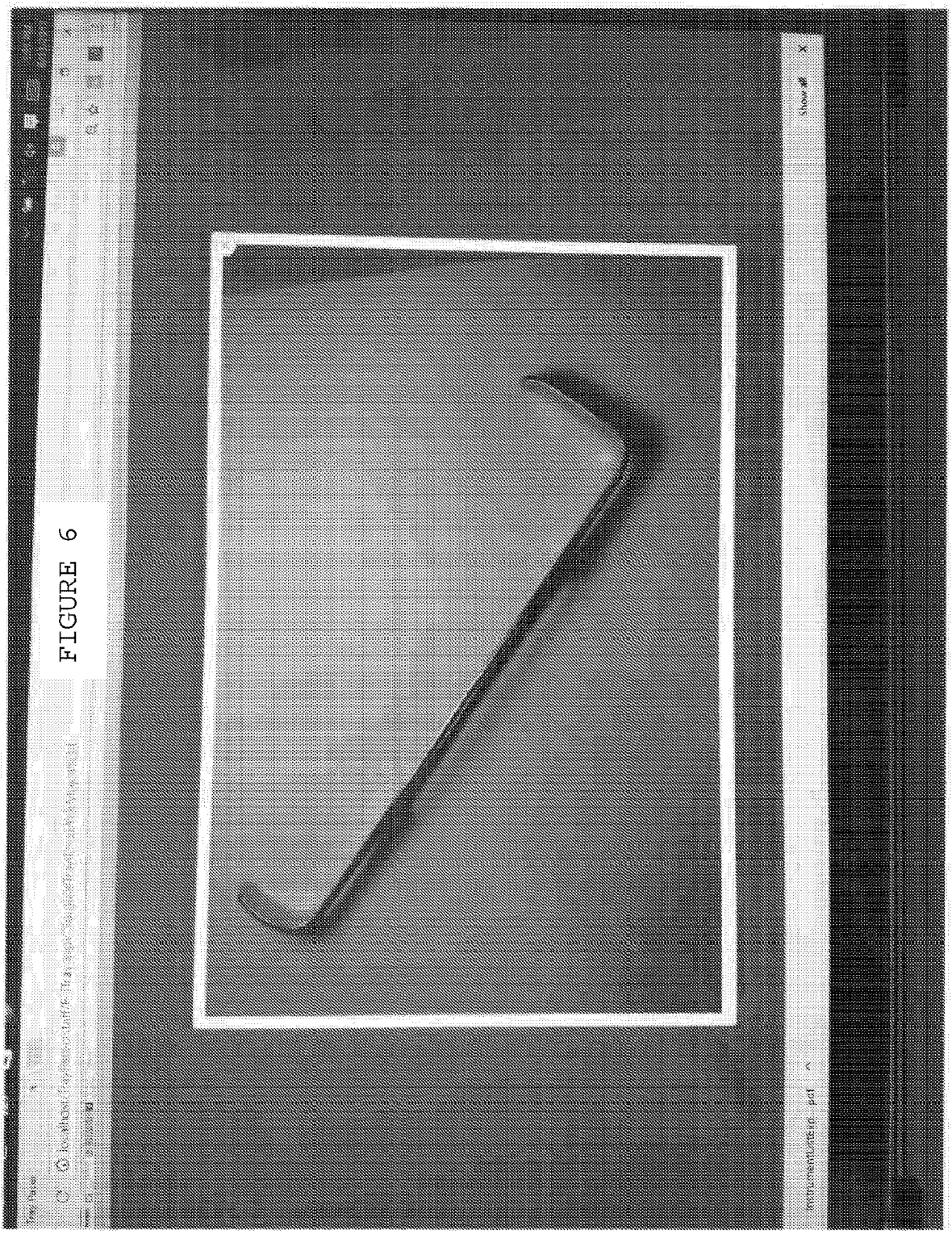
Figure 7:

As can be seen in FIG. 5, the active instrument to be placed in the tray is shown with one or more individual views that may be selected and enlarged. In this example, the retractor view includes three different views that may be selected for viewing. The individual views, for example, may be provided to show particular feature(s) of the instrument that have been pre-determined to aid in identification of the particular instrument. Further, the user may select one or more of the images for a larger view of the instrument as shown in FIG. 6. The image may be further zoomed and moved within a display window to see a close-up view of one or more portions of the instrument as shown in FIG. 7.

Once the user identifies and places the current instrument (Army-Navy Retractor, Double-Ended), the user can select the "add to tray" option to move onto the next instrument. The user also has an option to select a number of the selected instruments to the tray to identify how many instances of that particular instrument are being added via the "How Many X1" option.

Figure 8:
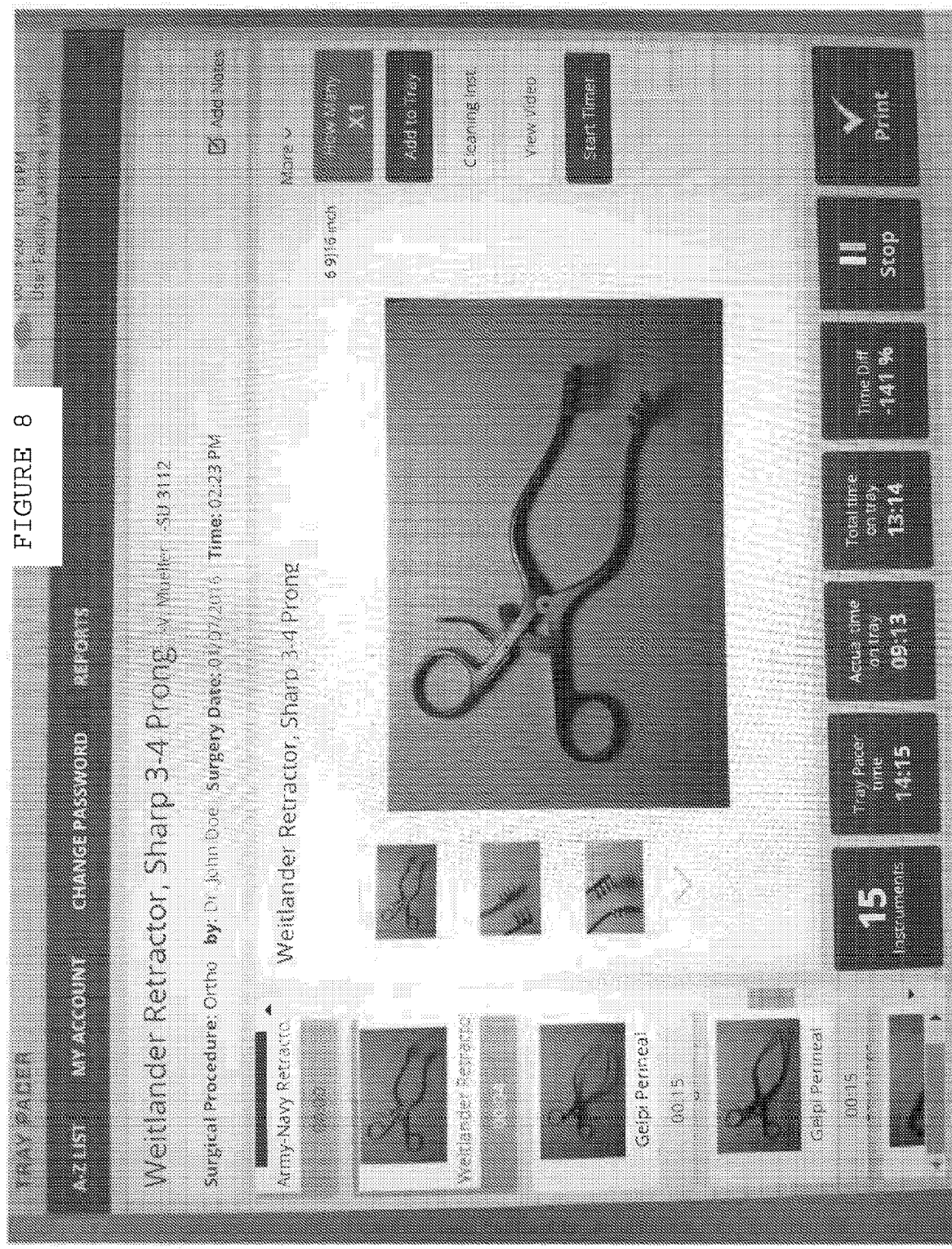
Figure 9:
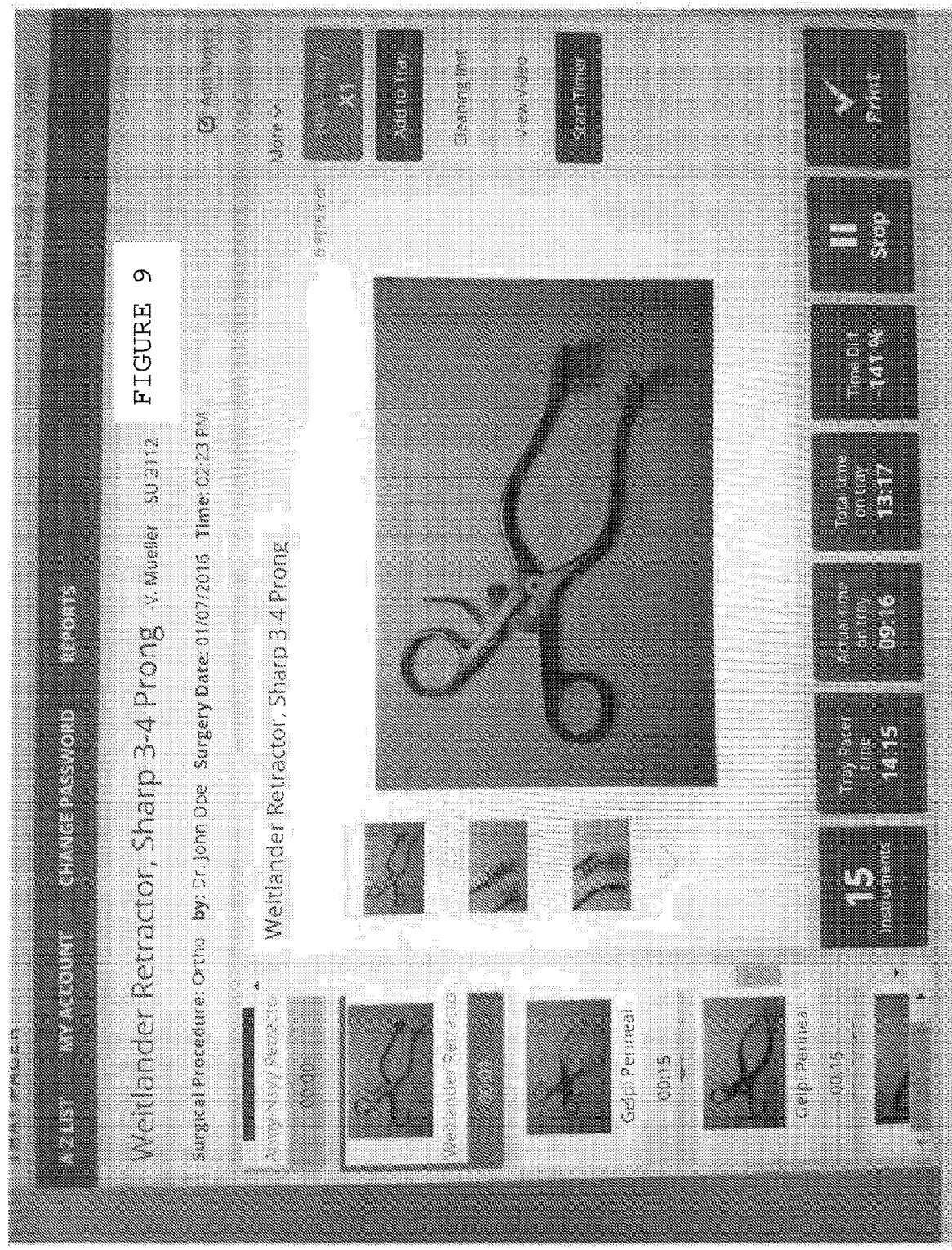

FIG. 8 shows the display of the next surgical instrument to be included added to the tray. In this example, the next instrument is a Weitland Retractor, Sharp 3-4 Prong. Again, the user interface shows that the prior instrument was not completed within a time limit and the system automatically advanced to the current retractor instrument. Also, in FIG. 9, as time is running out on the user to identify and add the instrument to the tray, the user interface shows that 00:01 seconds is remaining and the thumbnail associated with the current instrument changes states (e.g., turns red) indicating that the system is about to move to the next instrument in the list. At this time the user may choose to let the time run out and move to the next item if the instrument does not appear to be easily accessible or findable or may select the "Stop" option to pause the timers while the user takes additional time. In this example, the "actual time on tray" display may pause, while the "total time on tray" display may continue to count.

Although the example shown in FIGS. 4-9 show one example implementation where a user is directly comparing one or more pre-selected images of the instruments of interest to one or more actual instruments. The system may also include a camera element coupled to the computer system to take one or more images of an instrument placed in the view of the camera by the user. The system may analyze the image via one or more image processing algorithms to identify the instrument, eliminate the instrument, or make one or more suggestions to the user concerning the instrument displayed or the instrument to be found.

Figure 10:
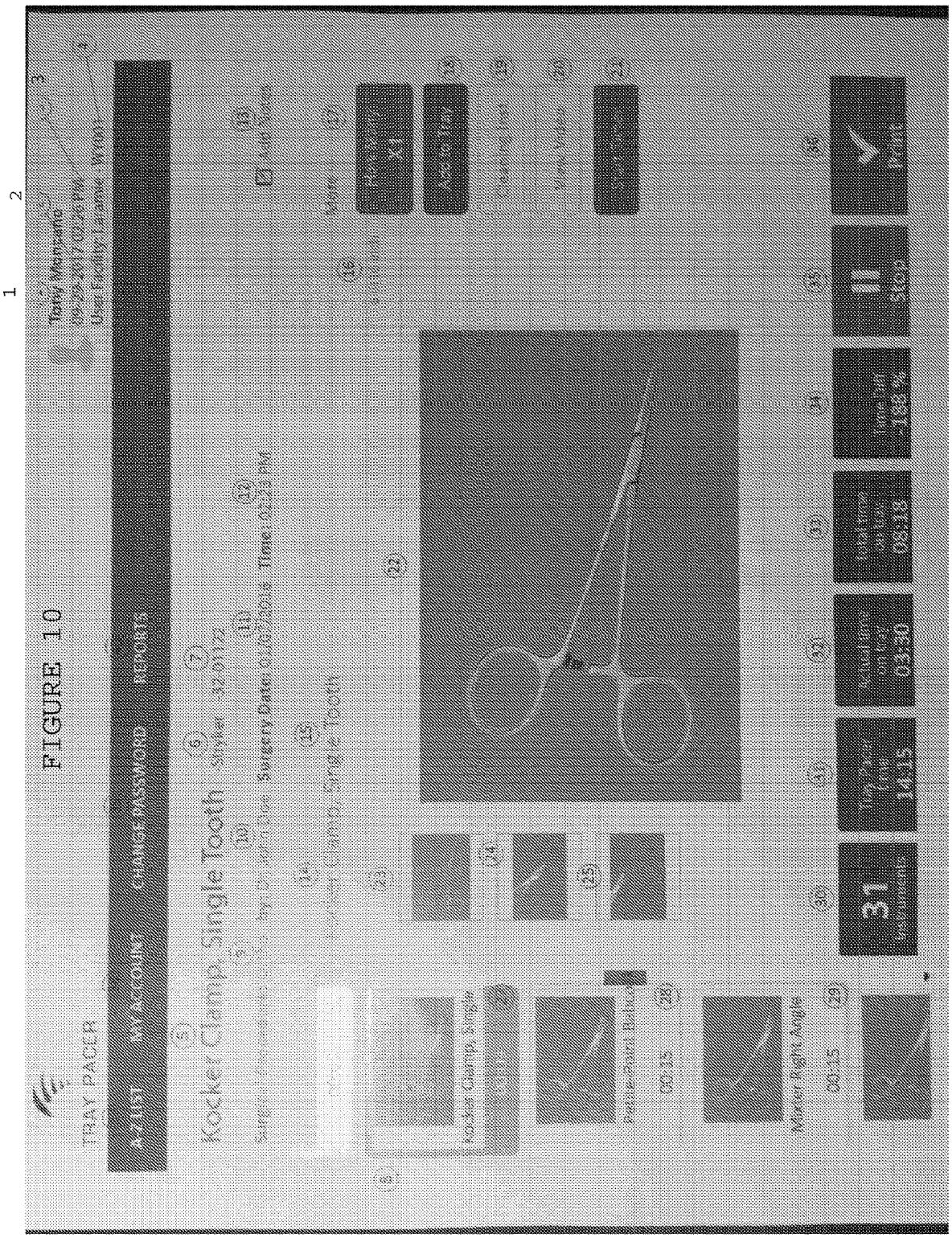
FIG. 10 shows an example screen shot of a computer-assisted collection assembly workstation.

FIG. 10 shows an example screen shot of a computer-assisted collection assembly workstation. In this particular implementation, for example, the screen shot includes the following items. (1) A name of a logged-in user. (2) A date of the log in. (3) A time of the log in. (4) An identifier of the facility that may include a specific identifier of that facility within a state or other geographic region. (5) A name of an instrument. (6) A maker/manufacturer of the instrument. (7) A manufacturer or other identifier for the instrument. (8) A scrollable list of each instrument and accessory to be included in a predetermined tray collection. In various implementations, for example, each item in the scrollable list of instruments includes an image that can be displayed on the full size image (22) shown for the instrument currently being added to the collection. The scrollable "prompt" list includes windows that can have a frame that changes colors or other aspects when the system is in operation to provide one or more instrument status. For example, the frame may be depicted in white when the instrument is part of the list still to be added to a tray, yellow when the instrument has been added to the tray, green when the item is being looked for, flashing red when the time allocated is about to expire (e.g., a three second warning), and solid red when the instrument has not been found or has not been added to the tray. When the last item has been found, the operator can then go back through the scrollable list and address the red framed items to complete the tray assembly. Once each of the items has been found (and show a green frame in the scrollable list), the process can close and finalize, such as with a printable report. (9) An identifier for an intended procedure for which the instrument tray applies. (10) A name of a surgeon or surgical team member assigned to the tray. (11) A date on which an operating room schedule states the procedure will take place according to an operating room requisition. (12) A time of the procedure per the operating room (OR) requisition. (13) The operator/packer is able to add a note to inform OR personnel or management, such as to identify an authorized exception to the exclusion, substitution, different manufacturer, or the like, for a particular instrument on an OR requisition. If a particular type of instrument is not available for whatever reason, the operator/packer can inform the OR team or management that the exclusion was authorized (e.g., by a specifically named person). (14) An industry name of an instrument. (15) An identifier of a special feature (e.g., identifying feature) of a particular instrument, such as but not limited to length, width, weight, different tip design or the like. (16) A length of the instrument. (17) A listing or other identifier of acceptable alternate instruments (e.g., if alternate manufacturers are acceptable, if authorized exemptions have been granted and by whom, inform the packer if the surgeon (10) requires anything special about the contents of the tray collection, and possible unacceptable substitutions). (18) A tab for the operator/packer to confirm that the correct instrument has been identified and added to the tray. Clicking this tab can also bring the next instrument to be addressed to the main display from the scrollable list. (19) A cleaning instruction tab that may be used for providing any procedures necessary for processing/cleaning the instrument. In various implementations, information may be presented in any number of formats such as a pop-up display including text, video or other formatted information, a print option for printing the information in a hardcopy format or the like. (20) A video tab for providing information relevant to the instrument. For example, where the instrument may be disassembled for cleaning, video or other formatted information may be provided upon selection of the tab to assist in assembly or disassembly of the instrument. This may be particularly helpful where instruments include unexpected parts to render the instrument functional. (21) A Start Timer tab that activates the process of assembling/filling a tray with the predetermined surgical instruments and, in some implementations, triggers a clock (33) to activate. (22) A main, enlarged image display of the instrument to be added to the tray collection. In some implementations, for example, the display may be pinched/zoomed to enlarge and scroll across the image to better show detail of the surgical instrument. Further, picture-in-picture or other close-up or zoomed out features may be provided as part of the display (22). (23) through (25) Thumbnail photos of different views of the instrument. (26) through (29) frames that may include variations in color or other features to identify statuses of the particular instruments in the scrollable list such as described above with reference to (8). For example, as the instruments are marked as "Add to Tray" (18), the scrolling prompt list (8) may move with the progress through the scrollable list. The operator/packer may be able to move/scroll through the list (8), such as if they have concerns about the instruments that have been added, that have been skipped or might have been added or skipped further down the scrollable list. The operator/packer can also go back through the scrollable list to confirm that he or she has found a missing item in the list (e.g., a red framed item) which they can add at the end or during the run. (30) When the program is active, the tab will show the total number of items to be included in the particular tray collection being assembled. As each item is added/confirmed to the list, the tab may be decremented to show the remaining number of instruments to be added. (31) A Tray Pacer timer tab informs the operator/packer how much time is ideally allotted for the tray to be completely finished. In some implementations, for example, the number may be set by a manager or calculated by the system based on history and may also be changed if circumstances dictate. (32) An actual time on tray tab shows the operator/packer how much time they have spent in the actual tray packing process. Time taken to deal with problems, breaks, etc. may not be included in this measure. (33) A total time on tray tab records the total time taken from the time the start timer tab is selected until the finished/print tab (36) is selected signifying the tray has been completed. (34) A time difference tab indicates the proficiency of the operator/packer to meet the expected time allotted to pack the particular tray. In the example shown, a percentage takes into account the indications shown in (32) and (33) and is meaningful when the tray is marked as complete (36). This measure, for example, may be useful in comparing the performance of different operators/packer and for measuring the progress of trainees. (35) A stop tab that may be used to stop the clock from advancing to another instrument while a different unrelated action takes place (e.g., retrieving further loads of instruments to be analyzed, having difficulty locating the instrument, seeking advice from a supervisor or colleague, etc.). This tab may change to "Start" or "Restart," for example, to indicate to the operator/packer to continue the packing process. (36) A Print/Complete tab is provided to stop the entire cycle indicating that the tray is complete. If there are items yet to be found (e.g., red framed in the scrolling list), the system may prevent the tray from being closed. If there are cautionary warnings (e.g., yellow framed in the scrolling list (8) with explanatory notes), the Print/Complete tab may be activated to indicate that the tray is complete. A printed and barcoded report can be issued and attached to the completed tray. (37) An A-Z List may provide an alphabetical listing of each tray used by the facility (e.g., by pull down menu or pop up window). (38) A My Account portal that provides information for the operator/packer logged in and identified at (1). (39) A change password link may be provided to allow the user to change or confirm a password and may include appropriate security factors. The link may also enable a different operator/packer to log into the workstation to, for example, complete an already started tray collection. (40) A report tab may be used to provide access to a user portal that, for example, may provide a complete history (or recent history) of the operator/packer so that the operator/packer may self-audit his or her proficiency, performance and confirm improvement or indicate problems. Also, management may compile individual or facility-wide data on the performance of the whole SPD's operations.

Exemplary Computing System

Figure 11:
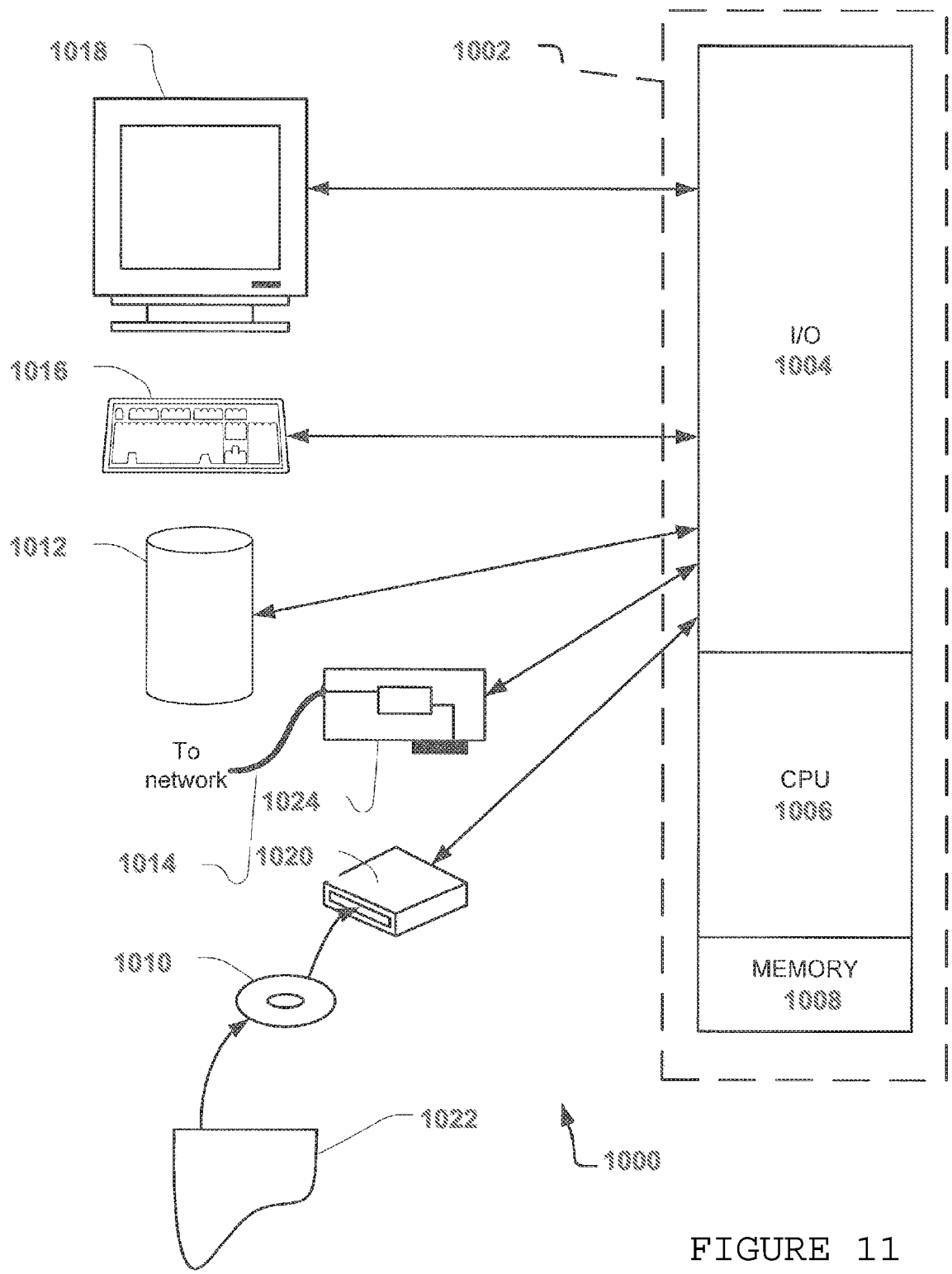
FIG. 11 shows a schematic diagram of an example computing device upon which a to camera-based and image-based methods and systems for accurately and efficiently assembling computer-assisted assembling and completing stocked or arranged disparate-shaped components of a collection using electronic images for identification may be implemented

FIG. 11 is a schematic diagram of an example computing device 1000 upon which a to camera-based and image-based methods and systems for accurately and efficiently assembling computer-assisted assembling and completing stocked or arranged disparate-shaped components of a collection using electronic images for identification may be implemented. As discussed herein, implementations include various steps. A variety of these steps may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware.

FIG. 11 illustrates an exemplary system useful in implementations of the described technology. A general purpose computer system 1000 is capable of executing a computer program product to execute a computer process. Data and program files may be input to the computer system 1000, which reads the files and executes the programs therein. Some of the elements of a general purpose computer system 1000 are shown in FIG. 11 wherein a processor 1002 is shown having an input/output (I/O) section 1004, a Central Processing Unit (CPU) 1006, and a memory section 1008. There may be one or more processors 1002, such that the processor 1002 of the computer system 1000 comprises a single central-processing unit 1006, or a plurality of processing units, commonly referred to as a parallel processing environment. The computer system 1000 may be a conventional computer, a distributed computer, or any other type of computer. The described technology is optionally implemented in software devices loaded in memory 1008, stored on a configured DVD/CD-ROM 1010 or storage unit 1012, and/or communicated via a wired or wireless network link 1014 on a carrier signal, thereby transforming the computer system 1000 in FIG. 11 into a special purpose machine for implementing the described operations.

The I/O section 1004 is connected to one or more user-interface devices (e.g., a keyboard 1016 and a display unit 1018), a disk storage unit 1012, and a disk drive unit 1020. Generally, in contemporary systems, the disk drive unit 1020 is a DVD/CD-ROM drive unit capable of reading the DVD/CD-ROM medium 1010, which typically contains programs and data 1022. Computer program products containing mechanisms to effectuate the systems and methods in accordance with the described technology may reside in the memory section 1008, on a disk storage unit 1012, or on the DVD/CD-ROM medium 1010 of such a system 1000. Alternatively, a disk drive unit 1020 may be replaced or supplemented by a floppy drive unit, a tape drive unit, or other storage medium drive unit. The network adapter 1024 is capable of connecting the computer system to a network via the network link 1014, through which the computer system can receive instructions and data embodied in a carrier wave. Examples of such systems include SPARC systems offered by Sun Microsystems, Inc., personal computers offered by Dell Corporation and by other manufacturers of Intel-compatible personal computers, PowerPC-based computing systems, ARM-based computing systems and other systems running a UNIX-based or other operating system. It should be understood that computing systems may also embody devices such as Personal Digital Assistants (PDAs), mobile phones, gaming consoles, set top boxes, etc.

When used in a LAN-networking environment, the computer system 1000 is connected (by wired connection or wirelessly) to a local network through the network interface or adapter 1024, which is one type of communications device. When used in a WAN-networking environment, the computer system 1000 typically includes a modem, a network adapter, or any other type of communications device for establishing communications over the wide area network. In a networked environment, program modules depicted relative to the computer system 1000 or portions thereof, may be stored in a remote memory storage device. It is appreciated that the network connections shown are exemplary and other means of and communications devices for establishing a communications link between the computers may be used.

In accordance with an implementation, software instructions and data directed toward operating the subsystems may reside on the disk storage unit 1012, disk drive unit 1020 or other storage medium units coupled to the computer system. Said software instructions may also be executed by CPU 1006.

The implementations described herein are implemented as logical steps in one or more computer systems. The logical operations are implemented (1) as a sequence of processor-implemented steps executing in one or more computer systems and (2) as interconnected machine or circuit modules within one or more computer systems. The implementation is a matter of choice, dependent on the performance requirements of a particular computer system. Accordingly, the logical operations making up the embodiments and/or implementations described herein are referred to variously as operations, steps, objects, or modules. Furthermore, it should be understood that logical operations may be performed in any order, unless explicitly claimed otherwise or a specific order is inherently necessitated by the claim language.

Furthermore, certain operations in the methods described above must naturally precede others for the described method to function as described. However, the described methods are not limited to the order of operations described if such order sequence does not alter the functionality of the method. That is, it is recognized that some operations may be performed before or after other operations without departing from the scope and spirit of the claims.

Although implementations have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

The invention claimed is:

1. A camera-based system for assembling and completing a collection of disparate shaped individual components with identification via electronic images, the system comprising:

a camera adapted to generate one or more digital images of one or more disparate shaped components placed within a field of view;

a processor configured to compare data associated with the one or more digital images generated by the camera to stored data associated with one or more digital images of a plurality of target components to be included in the collection, wherein the processor is configured to identify at least one of the target components if the data associated with the one or more digital images generated by the camera correspond to the stored data associated with a predetermined target component, wherein the processor is configured to identify an individual target component within a group of target components having a common type by identifying at least one feature unique to the individual target component within the group of target components, the one or more disparate shaped components comprise a plurality of surgical instruments and the at least one feature unique to the individual target component within the group of target components comprises at least one of a length, a width, a weight, and a tip design.

2. The system of claim 1 wherein the processor is adapted to process the one or more digital images generated by the camera to generate the data associated with the one or more digital images generated by the camera and compare data to the stored data.

3. The system of claim 2 wherein the stored data comprise identification information unique to each of the target components with respect to a plurality of available components.

4. A camera-based system for assembling and completing a collection of disparate shaped individual components via electronic images, the system comprising:

a camera adapted to generate one or more digital images of one or more disparate shaped components placed within a field of view;

a processor adapted to execute one or more software programs to:

identify at least one of a plurality of disparate shaped components based on at least one of the digital images, sort the disparate-shaped components and compare component images of the identified components to a requisition list, and selectively place the identified components corresponding to the requisition list in a specific receptacle, wherein the processor is configured to identify an individual target component within a group of target components having a common type by identifying at least one feature unique to the individual target component within the group of target components, the one or more disparate shaped components comprise a plurality of surgical instruments and the at least one feature unique to the individual target component within the group of target components comprises at least one of a length, a width, a weight, and a tip design.

5. A camera-based system for assembling and completing a collection of disparate shaped individual components via electronic images, the system comprising:

a camera adapted to generate one or more digital images of one or more disparate shaped components placed within a field of view;

a processor adapted to execute one or more software programs to:

provide computer-assisted identification to an operator to identify at least one of a plurality of disparate shaped components based on at least one of the digital images, provide computer-assisted sorting of the disparate-shaped components and comparing of component images of the identified components to a requisition list, and selectively designate the identified components corresponding to the requisition list for a specific receptacle, wherein the processor is configured to identify an individual target component within a group of target components having a common type by identifying at least one feature unique to the individual target component within the group of target components, the one or more disparate shaped components comprise a plurality of surgical instruments and the at least one feature unique to the individual target component within the group of target components comprises at least one of a length, a width, a weight, and a tip design.

6. The system of claim 5 wherein the components comprise surgical instruments.

7. The system of claim 6 wherein the receptacle comprises a surgical tray collection for the surgical instruments.

8. The system of claim 5 wherein at least a portion of the identified disparate shaped components are provided to an instrument storage or a collection assembly station depending on whether the identified instruments are components of an active collection assembly.

9. The system of claim 6 wherein software instructions are adapted to decide at least one of the group comprising: whether to designate for storage, whether to schedule for assembly, whether to schedule when to assemble, and what collection to assemble based at least in part on inventory used in real time or stored inventory.

10. The system of claim 8 wherein the at least a portion of the identified disparate shaped components are provided to a collection assembly station where the identified instruments are listed as components of the active collection assembly.

11. The system of claim 10 wherein the at least a portion of the identified disparate shaped components are provided to the instrument storage where the identified instruments are not listed as components of the active collection assembly.

12. The system of claim 5 wherein an active collection assembly is identified based on at least one of the group comprising: a surgical schedule, a predicted surgical event, a pattern of prior surgical events, doctor operating room uses, doctor block times, past surgical patterns, past surgical experience, artificial intelligence related to past surgical patterns or past surgical experience.

13. The system of claim 5 wherein the computer assisted identification comprises providing a plurality of images corresponding to a plurality of the components for the collection.

14. The system of claim 13 wherein the plurality of images for the plurality of corresponding components comprise at least one distinguishing feature for each of the plurality of components for the collection.

15. The system of claim 5 wherein the computer assisted identification provides at least one metric for the operator assembling the collection.

16. The system of claim 15 wherein the metric comprises a time to complete assembly of the collection.

17. The system of claim 15 wherein the metric comprises a comparison of the time to complete assembly of the collection and a target time to complete assembly of the collection.

18. The system of claim 15 wherein the metric comprises an actual time assembling the collection and a total time from a start to a finish of assembling the collection.

\* \* \* \* \*